United States Patent
Feldman et al.

(10) Patent No.: US 9,526,775 B2
(45) Date of Patent: Dec. 27, 2016

(54) GLYCOENGINEERED OUTER MEMBRANE VESICLES AND USE THEREOF AS VACCINES

(71) Applicant: The Governors of the University of Alberta, Edmonton (CA)

(72) Inventors: Mario Feldman, Edmonton (CA); Nancy Price, Edmonton (CA); Fatima Garcia-Quintanilla, Seville (ES); Maria Veronica Ielmini, Buenos Aires (AR)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

(21) Appl. No.: 14/397,149

(22) PCT Filed: Apr. 26, 2013

(86) PCT No.: PCT/CA2013/050322
§ 371 (c)(1),
(2) Date: Oct. 24, 2014

(87) PCT Pub. No.: WO2013/159234
PCT Pub. Date: Oct. 31, 2013

(65) Prior Publication Data
US 2015/0118263 A1 Apr. 30, 2015

Related U.S. Application Data

(60) Provisional application No. 61/639,340, filed on Apr. 27, 2012.

(51) Int. Cl.
| | | |
|---|---|---|
| *A61K 39/00* | (2006.01) | |
| *A61K 39/09* | (2006.01) | |
| *C12N 15/52* | (2006.01) | |
| *C12P 19/04* | (2006.01) | |
| *A61K 39/02* | (2006.01) | |
| *C12N 15/70* | (2006.01) | |

(52) U.S. Cl.
CPC ......... *A61K 39/092* (2013.01); *A61K 39/0208* (2013.01); *C12N 15/52* (2013.01); *C12N 15/70* (2013.01); *C12P 19/04* (2013.01); *A61K 2039/55555* (2013.01); *A61K 2039/6018* (2013.01)

(58) Field of Classification Search
CPC .................................................... A61K 39/092
See application file for complete search history.

(56) References Cited

U.S. PATENT DOCUMENTS

2011/0274720 A1   11/2011   Wacker et al.

FOREIGN PATENT DOCUMENTS

| WO | 2008093165 A2 | 5/2008 |
| WO | 2009104074 A2 | 8/2009 |
| WO | 2010/108682 A1 | 9/2010 |

OTHER PUBLICATIONS

Asensio, CJA et al. "Outer membrane vesicles obtained from Bordetella pertussis Tohama expressing the lipid A deacylase PagL as a novel acellular vaccine candidate," Vaccine, Feb. 11, 2011, 29(8):1649-1656.
Feldman, MF et al. "Engineering N-linked protein glycosylation with diverse O antigen lipopolysaccharide structures in *Escherichia coli*." PNAS, Feb. 22, 2005, 102(8):3016-3021.
Chen, DJ et al. "Delivery of foreign antigens by engineered outer membrane vesicle vaccines." PNAS, Feb. 16, 2010, 107(7):3099-3104.
Gebhart, C. et al. "Characterization of exogenous bacterial oligosaccharyltransferases in *Escherichia coli* reveals the potential for O-linked protein glycosylation in Vibrio cholerae and Burkholderia thailandensis." Glycobiology, Mar. 5, 2012, 22(7):962-974.
Written Opinion and International Search Report of related PCT/CA2013/050322 mailed Jul. 24, 2013.
International Preliminary Report on Patentability (Chapter I) of related PCT/CA2013/050322 issued Oct. 28, 2014.
Arnold, R et al. "Effectiveness of a vaccination programme for an epidemic of meningococcal B in New Zealand." Vaccine, Sep. 16, 2011, 29(40):7100-7106.
Haurat, MF et al. "Selective sorting of cargo proteins into bacterial membrane vesicles." JBC, Jan. 14, 2011, 286 (2):1269-1276.
Hug I et al. "Exploiting Bacterial Glycosylation Machineries for the Synthesis of a Lewis Antigen-containing Glycoprotein." JBC, Oct. 28, 2011, 288(43):37887-37894.
Kim J-Y et al. "Engineered Bacterial Outer Membrane Vesicles with Enhanced Functionality." J. Mol. Biol. Jun. 27, 2008, 380(1):51-86.
Koeberling O et al. "Bactericidal Antibody Responses Elicited by a Meningococcal Outer Membrane Vesicle Vaccine with Overexpressed Factor H-Binding Protein and Genetically Attenuated Enotoxin." JID, Jul. 15, 2008, 198 (2):262-270.
Koeberling O, et al. "Meningococcal Outer Membrane Vesicle Vaccines Derived from Mutant Strains Engineered to Express Factor H Binding Proteins from Antigenic Variant Groups 1 and 2." Clin Vaccine Immunol. Feb. 2009, 16(2):156-162.
Kulp A and Kuehn MJ. "Biological functions and biogenesis of secreted bacterial outer membrane vesicles." Annu Rev Microbiol. 2010, 64:163-184.

(Continued)

Primary Examiner — Albert Navarro
(74) Attorney, Agent, or Firm — Polsinelli PC

(57) ABSTRACT

The present application relates to glycoengineered outer membrane vesicles obtained from recombinant, gram-negative bacteria comprising hetereologous DNA encoding an enzyme or enzymes that produce a heterologous glycan that replaces all or a portion of the naturally-occurring O antigen in the lipopolysaccharides of the bacteria. Also provided by the present application are immunogenic compositions and vaccines prepared from the glycoengineered outer membrane vesicles expressing the heterologous glycans at their surface.

8 Claims, 14 Drawing Sheets

(56) References Cited

OTHER PUBLICATIONS

Van De Waterbeemd B et al. "Improved OMV vaccine against Neisseria meningitidis using genetically engineered strains and a detergent-free purification process." Vaccine, Jul. 5, 2010, 28(30):4810-4816.

European Search Report and Written Opinion, Application No. EP 13782478, dated Nov. 12, 2015, 16 pages.

Faridmoayer et al., "Extreme Substrate Promiscuity of the Neisseria Oligosaccharyl Transferase Involved in Proteir O-Glycosylation," The Journal of Biological Chemistry, 2008, pp. 34596-34604, vol. 283, No. 50.

Fisher et al., "Production of Secretory and Extracellular N-Linked Glycoproteins in *Escherichia coli*," Applied and Environmental Microbiology, 2011, pp. 811-881, vol. 77, No. 3.

Henderson et al., "Site-Specific Modification of Recombinant Proteins: A Novel Platform for Modifying Glycoproteins Expressed in *E coli*." Bioconjugate Chemistry, 2011, pp. 903-912, vol. 22.

Office Action from related Canadian Patent Application No. 2,894,795 dated Apr. 27, 2016, 5 pages.

Endicott, "Engineering *Escherichia coli* for Novel Vesicle Vaccine Methods", Thesis presented to Cornell University, Aug. 2010, 48 pages.

Third Party Obervations from related EP Application No. 13782478.5 dated Jun. 24, 2016, 11 pages.

cps locus of S. pneumoniae serotype 14 (CPS14)

Rabbit + = positive control, pneumococcal serotype 14 polyclonal rabbit sera
CTRL = OMV+VC injected sera
G2, G3 = OMV+CPS14 injected sera

Streptococcus = pNLP80
Burkholderia = pEQ3
Campylobacter = pACYCpglBmut
VC = vector control
glycan = plasmid expressing bacterial capsule/OPS

SEQUENCE LISTING

```
<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Forward primer

<400> SEQUENCE: 1
atagagctca tggataaaaa aggattggaa at                                 32

<210> SEQ ID NO 2
<211> LENGTH: 23
<212> TYPE: DNA
<213> ORGANISM: Artificial Sequence
<220> FEATURE:
<223> OTHER INFORMATION: reverse primer

<400> SEQUENCE: 2
ttaagaaatt catcctcata caa                                           23

<210> SEQ ID NO 3
<211> LENGTH: 23
<212> TYPE: DNA
<213> ORGANISM: Artificial Sequence
<220> FEATURE:
<223> OTHER INFORMATION: Forward primer

<400> SEQUENCE: 3
ctggtcaaca aatattagaa aaa                                           23

<210> SEQ ID NO 4
<211> LENGTH: 32
<212> TYPE: DNA
<213> ORGANISM: Artificial Sequence
<220> FEATURE:
<223> OTHER INFORMATION: reverse primer

<400> SEQUENCE: 4
atactcgaga ttctttctgt aaactccaaa aa                                 32
```

GLYCOENGINEERED OUTER MEMBRANE VESICLES AND USE THEREOF AS VACCINES

This application is the national phase of International Application No. PCT/CA2013/050322, filed Apr. 26, 2013, entitled "Glycoengineered Outer Membrane Vesicles And Use Thereof As Vaccines," which claims the benefit of U.S. Provisional Application No. 61/639,340, filed Apr. 27, 2012, entitled, "Glycoengineered Outer Membrane Vesicles And Use Thereof As Vaccines," the disclosures of which are all incorporated here by reference in their entirety.

FIELD OF THE INVENTION

The present application pertains to the field of vaccines. More particularly, the present application relates to glycoengineered outer membrane vesicle vaccines.

BACKGROUND

All Gram negative bacteria studied to date are known to be able to produce outer membrane vesicles (OMVs) (Kulp A, Kuehn M J. Biological functions and biogenesis of secreted bacterial outer membrane vesicles. Annu Rev Microbiol; 64:163-84). Due to their immunogenic properties, self-adjuvanticity, ability to be taken up by mammalian cells, and capacity for enhancement by recombinant engineering, OMVs are attractive candidates for vaccine delivery platforms. The use of an OMV as a vaccine is exemplified by the MeNZB vaccine, which has been effectively and safely used against bacterial meningitis in New Zealand, leading to a drastic reduction in the incidence of this type of infection in the country (Arnold R, Galloway Y, McNicholas A, O'Hallahan J. Effectiveness of a vaccination programme for an epidemic of meningococcal B in New Zealand. Vaccine; 29(40):7100-6). OMVs have also been safely used in human vaccines used in Cuba, Brazil and Norway, among other countries. Several studies reported that OMV vaccines can protect mice from infection by *Bordetella pertussis, Salmonella typhimurium* and *Brucella melitensis*, among other pathogens (Asensio C J, Gaillard M E, Moreno G, Bottero D, Zurita E, Rumbo M, et al. Outer membrane vesicles obtained from *Bordetella pertussis* Tohama expressing the lipid A deacylase PagL as a novel acellular vaccine candidate. Vaccine 2011; 29(8):1649-56). It is generally believed that protection is due to the immunogenicity of certain outer membrane proteins found on the OMVs.

OMVs are mainly composed of lipopolysaccharide (LPS), outer membrane and periplasmic proteins and phospholipids, and are formed by blebbing of the outer membrane. LPS contains lipid A, also known as endotoxin, and generally, O antigen, which is a polysaccharide of variable structure. Previous efforts to engineer OMV were directed to manipulation of the protein content in OMV preparations (Chen D J, Osterrieder N, Metzger S M, Buckles E, Doody A M, DeLisa M P, et al. Delivery of foreign antigens by engineered outer membrane vesicle vaccines. Proc Natl Acad Sci USA 2010;107(7):3099-104; Kim J Y, Doody A M, Chen D J, Cremona G H, Shuler M L, Putnam D, et al. Engineered bacterial outer membrane vesicles with enhanced functionality. J Mol Biol 2008;380(1):51-66; Koeberling O, Giuntini S, Seubert A, Granoff DM. Meningococcal outer membrane vesicle vaccines derived from mutant strains engineered to express factor H binding proteins from antigenic variant groups 1 and 2. Clin Vaccine Immunol 2009;16(2):156-62; and van de Waterbeemd B, Streefland M, van der Ley P, Zomer B, van Dijken H, Martens D, et al. Improved OMV vaccine against *Neisseria meningitidis* using genetically engineered strains and a detergent-free purification process. Vaccine 2010;28(30):4810-6). Furthermore, work on engineering strains to produce OMV containing modified, less toxic, lipid A has been published (Asensio C J, Gaillard M E, Moreno G, Bottero D, Zurita E, Rumbo M, et al. Outer membrane vesicles obtained from *Bordetella pertussis* Tohama expressing the lipid A deacylase PagL as a novel acellular vaccine candidate. Vaccine 2011;29(8):1649-56 and Koeberling O, Seubert A, Granoff D M. Bactericidal antibody responses elicited by a meningococcal outer membrane vesicle vaccine with overexpressed factor H-binding protein and genetically attenuated endotoxin. J Infect Dis 2008;198(2):262-70).

Current vaccines against Gram positive bacteria, like *Streptococcus pneumoniae*, consist of chemically prepared conjugates comprising capsular polysaccharide chemically coupled to a protein carrier. Gram positive bacteria do not produce OMVs.

There remains a need for alternative OMV vaccines and OMV vaccines against Gram positive bacteria.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide glycoengineered outer membrane vesicles ("geOMV") and methods of manufacture and use thereof. The glycoengineered OMV comprise an OMV from a gram-negative bacteria engineered to produce one or more glycans that are not naturally produced from the gram-negative bacteria. When the one or more heterologous glycans are antigenic, these glycoengineered OMVs can be useful as vaccines. Described herein is a method to generate an immune response using glycoengineered OMV in which diverse carbohydrates, including, for example, O antigens from Gram negative and capsule from Gram positive bacteria, are expressed in a bacterium producing OMV, such as *Escherichia coli*. In one example, it was possible to exploit the similarities between capsule and O antigen synthesis to generate engineered *E. coli* cells packing capsule from Gram positive bacteria into OMV, to elicit an IgG immune response to the capsule glycan.

In accordance with an aspect of the present invention, there is provided a recombinant, gram-negative bacteria comprising hetereologous DNA encoding an enzyme or enzymes that produce a heterologous glycan, wherein the recombinant bacteria presents the heterologous glycan on its surface as a component of lipopolysaccharides (LPS) that replaces all or a portion of the naturally-occurring O antigen. The heterologous glycan can be one or more of the following:

oligosaccharide from N-glycosylated protein (e.g., *Campylobacter*);

oligosaccharide from O-glycosylated protein (e.g., *Acinetobacter baumanni, Neisseria* or *Pseudomonas*);

O antigen from a gram-negative bacteria (e.g., *Burkholderia pseudomallei*);

capsular polysaccharide from a gram-positive bacteria (e.g., *Staphylococcus aureus* or *Streptococcus pneumoniae*) or from a gram-negative bacteria (e.g., *Acinetobacter baumanni, Neisseria* or *Pseudomonas*);

synthetic or non-bacterial glycan (e.g., Lewis antigen, a glycan identified as an antigen on cancer cells, a glycan derived from a eukaryotic pathogen, such as a fungus, or a glycan derived from a viral pathogen); or a combination of one or more of the above.

In accordance with another aspect of the invention, there is provided an outer membrane vesicle obtained from recombinant, gram-negative bacteria comprising hetereologous DNA encoding an enzyme or enzymes that produce a heterologous glycan, wherein the recombinant bacteria presents the heterologous glycan on its surface as a component of lipopolysaccharides (LPS) that replaces all or a portion of the naturally-occurring O antigen, wherein the outer membrane vesicle expresses the heterologous glycan on its surface.

In accordance with another aspect of the invention, there is provided an immunogenic composition comprising outer membrane vesicles as described herein, that are obtained from recombinant, gram-negative bacteria comprising hetereologous DNA encoding an enzyme or enzymes that produce a heterologous glycan, wherein the recombinant bacteria presents the heterologous glycan on its surface as a component of lipopolysaccharides (LPS) that replaces all or a portion of the naturally-occurring O antigen, wherein the outer membrane vesicle expresses the heterologous glycan on its surface.

In accordance with another aspect of the invention, there is provided a vaccine comprising outer membrane vesicles as described herein, that are obtained from recombinant, gram-negative bacteria comprising hetereologous DNA encoding an enzyme or enzymes that produce a heterologous glycan, wherein the recombinant bacteria presents the heterologous glycan on its surface as a component of lipopolysaccharides (LPS) that replaces all or a portion of the naturally-occurring O antigen, wherein the outer membrane vesicle expresses the heterologous glycan on its surface.

In accordance with another aspect of the invention, there is provided a use of an immunogenic composition or vaccine, as described herein, to inoculate a subject against a pathogenic bacteria, wherein the heterologous glycan is derived from the pathogenic bacteria.

In accordance with another aspect of the invention, there is provided a method of raising an immune response in a mammal comprising administering to the mammal glycoengineered outer membrane vesicles, optionally in an immunogenic composition or a vaccine as described herein.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION

Figure 1A:
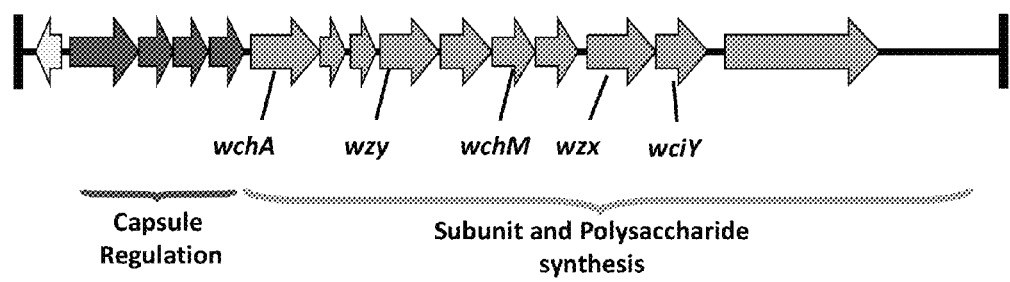
FIG. 1A schematically depicts the repeating glycan unit of CPS14.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The term "glycan" is used herein to refers to a polysaccharide or oligosaccharide, or to the carbohydrate portion of a glycoconjugate, such as a glycoprotein. Glycans can be homo- or heteropolymers of monosaccharide residues, and can be linear or branched.

The term "lipopolysaccharides" (LPS) is well known to refer to lipoglycans that are typically found in the outer membrane of Gram-negative bacteria and act as endotoxins and/or elicit strong immune responses in animals. LPS are made up of three components: the O antigen (or O polysaccharide), the core polysaccharide and lipid A. The O antigen is the outermost domain of the LPS and is a repetitive glycan polymer.

The term "glycoengineered" when used herein to refer to an organism or OMV, indicates that the organism, or OMV as produced from an organism, has been modified to produce a glycan, which can be part of LPS, capsule, glycolipids or glycoproteins, that differs from the naturally occurring glycan in the native organism or OMV, for example, in terms of structure, location and/or level of production.

The term "OMV vaccine" as used herein, refers to a vaccine consisting of, or comprising, an OMV that displays one or more antigenic proteins, glycoproteins or glycans, that is capable of eliciting an immune response in an animal or human.

The term "heterologous" antigen as used herein, refers to an antigen derived from a species or source, such as a pathogenic species, that is different from the species of bacterium from which the OMV is obtained, and is preferably a glycan antigen from a pathogen genus different from the genus of bacterium from which the OMV is obtained.

The present disclosure provides glycoengineered OMV. These glycoengineered OMV can be used to elicit an immune response in an animal or human, for example, in use as a vaccine. This disclosure further provides an immunogenic composition comprising glycoengineered OMV, displaying an immunogenic glycan. The immunogenic composition is useful for inducing production of antibodies for diagnostic and therapeutic purposes. This disclosure further provides an inoculum and vaccine comprising the immunogenic composition dispersed or dissolved in a pharmaceutically acceptable diluent.

The glycoengineered OMV can display one or more of the following heterologous glycans:
  oligosaccharide from N-glycosylated protein (e.g., *Campylobacter*);
  oligosaccharide from O-glycosylated protein (e.g., *Acinetobacter baumanni, Neisseria* or *Pseudomonas*);
  O antigen from a gram-negative bacteria (e.g., *Burkholderia pseudomallei*);
  capsular polysaccharide from a gram-positive bacteria (e.g., *Staphylococcus aureus* or *Streptococcus pneumoniae*) or from a gram-negative bacteria (e.g., *Acinetobacter baumanni, Neisseria* or *Pseudomonas*);
  synthetic or non-bacterial glycan (e.g., Lewis antigen, a glycan identified as an antigen on cancer cells, a glycan derived from a eukaryotic pathogen, such as a fungus, or a glycan derived from a viral pathogen); or
  a combination of one or more of the above.

LPS is the major component of the outer membrane of Gram-negative bacteria and are also found as a major component of OMV. As described above, LPS is made up of three components, with the O antigen being the polysaccharide that is displayed from the outer surface of the outer membrane of the Gram-negative bacteria or OMV. It has now been found that it is possible to engineer gram-negative bacteria to produce OMV in which the LPS component includes a heterologous glycan in place of the naturally occurring O antigen. Accordingly, in accordance with one aspect of the present application, there is provided a glycoengineered OMV comprising a heterologous glycan in place of the naturally occurring O antigen. Also provided is a method of manufacturing a glycoengineered OMV comprising genetically engineering an OMV-producing, gram-negative bacteria to produce LPS displaying a heterologous glycan in place of the naturally-occurring O antigen.

Heterologous O Antigen

In one embodiment, there is provided a glycoengineered OMV expressing an O antigen from a bacterium that differs from the bacterium producing the OMV (i.e., a non-host bacterial O antigen). In accordance with a related embodiment, there is provided a method of generating a glycoengineered OMV comprising genetically engineering an OMV-producing, gram-negative bacteria to produce LPS having a non-native O antigen, wherein the non-native O antigen is from a second gram-negative bacteria (for example, a pathogenic bacteria). In one embodiment, the host bacteria are transformed to include DNA encoding enzymes responsible for production of the non-native O antigen. The DNA encoding these enzymes optionally includes an inducible promoter sequence. Further, the host bacteria can be engineered to be deficient in production of its native O antigen.

In one embodiment there is provided a glycoengineered OMV that displays a heterologous O-antigen. In a specific example of this embodiment, the O-antigen is derived from *Burkholderia pseudomallei*.

Capsular Polysaccharide

Polysaccharide encapsulated bacteria, are a group of bacteria that have an outer polysaccharide covering referred to as a bacterial capsule. The encapsulated bacteria can be either Gram-negative or Gram-positive. Often, encapsulated bacterial are pathogenic and, as a result, vaccines have been developed based on antigenic response to the capsular polysaccharide. As a result, the present application also provides glycoengineered OMV that display a capsular polysaccharide on its surface. It is important to recognize that naturally occurring OMV do not include capsules. However, by engineering the Gram-negative bacteria to treat the capsular polysaccharide as an O antigen it is possible to display the capsular polysaccharide on the surface of the OMV.

In accordance with one aspect of the present application, there is provided a glycoengineered OMV displaying on its surface a capsular polysaccharide. In one embodiment, the capsular polysaccharide is derived from a Gram-negative bacterium. In an alternative embodiment, the capsular polysaccharide is derived from a Gram-positive bacterium.

In accordance with another aspect, there is provided a method of producing a glycoengineered OMV that displays on its surface a capsular polysaccharide. The method comprises genetically engineering an OMV-producing, gram-negative bacteria to express LPS having a capsular polysaccharide in place of the naturally-occurring O antigen. In this method, the OMV-producing, gram-negative host bacteria has been genetically modified such that it does not generate the naturally-occurring O antigen. Further, the host bacterium is transformed to include DNA encoding the enzymes responsible for production of the capsular polysaccharide. The DNA encoding these enzymes optionally includes an inducible promoter sequence.

In accordance with one embodiment, the host gram-negative bacteria is engineered such that it includes the following components (a) DNA encoding the enzymes responsible for producing the capsular polysaccharide; and, optionally, (b) DNA comprising genes encoding proteins required for the assembly of the capsular polysaccharide onto a lipid carrier. The lipid carrier is typically a polyprenol-pyrophosphate including, but not limited to, undecaprenol-pyrophosphate.

In order for the capsular polysaccharide to be displayed on the surface of the OMV, it must be capable of assembly on a lipid carrier, such as undecaprenol pyrophosphate, for transfer via a ligase to a lipid A.

In one embodiment there is provided a glycoengineered OMV that displays a capsular polysaccharide. The polysaccharide can be derived from a Gram-positive bacteria. In a specific example of this embodiment, the OMV-displayed capsular polysaccharide is derived from *Staphylococcus aureus* or *Streptococcus pneumoniae*. Alternatively, the polysaccharide can be derived from a Gram-negative bacteria. In a specific example of this embodiment, the OMV-displayed capsular polysaccharide is derived from a *Neisseria, Acinetobacter baumannii* or *Pseudomonas*.

Glycan from N-Glycosylated and O-Glycosylated Protein

In conjugate vaccine production, glycoproteins have been used as vaccines to help elicit an immune response and provide protection against various pathogens and other ailments. In these vaccines, the attachment of glycans to proteins helps increase the immunogenicity of the glycans.

In accordance with one aspect of the present application, Gram-negative bacteria can be engineered to express the glycosidic portion of an N- or O-glycosylated protein in place of the naturally-occurring O antigen component of LPS. As a result the glycosidic portion of the N- or O-glycosylated protein will be displayed on the surface of the engineered bacterium as well as the OMV produced from the bacterium.

In accordance with one aspect of the present application, there is provided a glycoengineered OMV displaying on its surface a glycosidic portion of an N- or O-glycosylated protein.

In accordance with another aspect, there is provided a method of producing a glycoengineered OMV that displays on its surface a glycosidic portion of an N- or O-glycosylated protein. The method comprises genetically engineering an OMV-producing, gram-negative bacteria to express LPS having a glycosidic portion of an N- or O-glycosylated protein in place of the naturally-occurring O antigen. In a preferred embodiment of this method, the OMV-producing, gram-negative host bacteria has been genetically modified such that it does not generate the naturally occurring O antigen. Further, the host bacterium is transformed to include DNA encoding the enzyme(s) responsible for production of the glycosidic portion of an N- or O-glycosylated protein. The DNA encoding these enzyme(s) optionally includes an inducible promoter sequence.

In accordance with one embodiment, the host gram-negative bacteria is engineered such that it includes the following components (a) DNA encoding the enzyme(s) responsible for producing the glycosidic portion of an N- or O-glycosylated protein; and, optionally, (b) DNA comprising genes encoding proteins required for the assembly of the glycosidic portion of an N- or O-glycosylated protein onto a lipid carrier. The lipid carrier is typically a polyprenol-pyrophosphate including, but not limited to, undecaprenol-pyrophosphate.

In order for the glycosidic portion of an N- or O-glycosylated protein to be displayed on the surface of the OMV, it must be capable of assembly on a lipid carrier, such as undecaprenol pyrophosphate, for transfer via a ligase to a lipid A.

In one embodiment there is provided a glycoengineered OMV that displays a glycosidic portion of an N-glycosylated protein. In a specific example of this embodiment, the glycan of the N-glycosylated protein is derived from a *Campylobacter*, including *Campylobacter jejuni* and *Campylobacter fetus venerealis*.

In one embodiment there is provided a glycoengineered OMV that displays a glycosidic portion of an O-glycosylated protein. In a specific example of this embodiment, the glycan of the O-glycosylated protein is derived from *Acinetobacter baumannii, Neisseria* or *Pseudomonas*.

Synthetic or Non-Bacterial Glycan

There are many examples of antigenic glycans associated with non-bacterial pathogens, cancer cells, blood cells, etc. In accordance with one aspect of the present application, there is provided there is provided a glycoengineered OMV displaying on its surface a synthetic or non-bacterial glycan.

In accordance with another aspect, there is provided a method of producing a glycoengineered OMV that displays on its surface a synthetic or non-bacterial glycan. The method comprises genetically engineering an OMV-producing, gram-negative bacteria to express LPS having the synthetic or non-bacterial glycan in place of the naturally-occurring O antigen.

In the embodiment in which the glycan is derived from a eurkaryotic source the Gram-negative bacterium is engineered to express the appropriate set of glycosyltransferases and sugar modified enzymes (see, for example, Hug, I. et al. *J. Biol. Chem.* 2011 286: 37887-37894, which is incorporated herein by reference in its entirety). Specific examples of such glycans are Lewis antigens, T antigens, sugars present in gangliosides and glycans normally present in human glycolipids, like GM1. In some instances, the glycoengineered OMV disclosed herein has been engineered to display a combination of heterologous antigenic glycans. For example, the OMV can display both a capsular polysaccharide and a glycan from an N- or O-glycosylated membrane protein. In some examples, where the glycoengineered OMV is to be used as a vaccine, the heterologous antigenic glycan and the heterologous antigenic protein are derived from the same organism, such as a pathogen.

OMV Vaccine

Also provided by the present application is a vaccine and a method for producing the vaccine, where the method comprises a) providing any of the engineered, or recombinant, host Gram-negative bacteria described above, and b) preparing an outer membrane vesicle (OMV) from the host bacteria. In one embodiment, the method further comprises c) isolating and/or purifying the outer membrane vesicle.

According to the present application, a vaccine is a preparation that can be administered to a subject to induce a humoral immune response (including eliciting a soluble antibody response) and/or cell-mediated immune response (including eliciting a cytotoxic T-lympocyte ("CTL") response). The vaccines provided herein comprise glycoengineered OMV and are effective in inducing an immune response against the OMV displayed glycan antigens and, if present, protein antigens. As a result the vaccines provided herein induce an immune response against the organism from which displayed glycan antigen and, when present, protein antigen are derived.

Vaccines can further contain an adjuvant. The term "adjuvant" as used herein refers to any compound which, when injected together with an antigen, non-specifically enhances the immune response to that antigen. Exemplary adjuvants include Complete Freund's Adjuvant, Incomplete Freund's Adjuvant, Gerbu adjuvant (GMDP; C.C. Biotech Corp.), RIBI fowl adjuvant (MPL; RIBI Immunochemical Research, Inc.), potassium alum, aluminum phosphate, aluminum hydroxide, QS21 (Cambridge Biotech), Titer Max adjuvant (CytRx), Cystine phosphate Guanine (CpG) and Quil A adjuvant. Other compounds that can have adjuvant properties include binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavouring agent such as peppermint, methyl salicylate or orange flavouring, and a coloring agent.

Vaccines can be formulated using a pharmaceutically acceptable diluent. Exemplary "diluents" include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose. Exemplary "carriers" include liquid carriers (such as water, saline, culture medium, saline, aqueous dextrose, and glycols) and solid carriers (such as carbohydrates exemplified by starch, glucose, lactose, sucrose, and dextrans, antioxidants exemplified by ascorbic acid and glutathione, and hydrolyzed proteins.

Vaccines can contain an excipient. The term "excipient" refers herein to any inert substance (e.g., gum arabic, syrup, lanolin, starch, etc.) that forms a vehicle for delivery of an antigen. The term excipient includes substances that, in the presence of sufficient liquid, impart to a composition the adhesive quality needed for the preparation of pills or tablets.

Vaccine of the present application can be lyophilised or in aqueous form, e.g., solutions or suspensions. Liquid formulations of this type allow the compositions to be administered directly from their packaged form, without the need for reconstitution in an aqueous medium, and are thus ideal for injection. Compositions can be presented in vials, or they can be presented in ready filled syringes. The syringes can be supplied with or without needles. A syringe will include a single dose of the composition, whereas a vial can include a single dose or multiple doses (e.g. 2 doses). In one embodiment the dose is for human. In a further embodiment the dose is for an adult, adolescent, toddler, infant or less than one year old human and can be administered by injection.

Where a vaccine requires reconstitution, there is provided a kit, which can comprise two vials, or can comprise one ready-filled syringe and one vial, with the contents of the syringe being used to reconstitute the contents of the vial prior to injection.

The vaccine can be formulated for administration by injection via the intramuscular, intraperitoneal, intradermal or subcutaneous routes; or via mucosal administration to the oral/alimentary, respiratory (e.g., intranasal administration), genitourinary tracts. Although the vaccine can be administered as a single dose, components thereof can also be co-administered together at the same time or at different times. In addition to a single route of administration, 2 different routes of administration can be used.

Another aspect of the application provides a method for immunizing a mammalian subject, comprising a) providing i) any of the vaccines described herein, and ii) a mammalian subject, and b) administering an immunologically effective amount of the vaccine to the subject to produce an immune response. In one embodiment, the immune response comprises bactericidal antibody production. In one embodiment, the method further comprises c) detecting the presence of bactericidal antibody. In a related aspect, there is provided a use of a glycoengineered OMV, as described above, to elicit an immune response in a mammalian subject.

To gain a better understanding of the invention described herein, the following examples are set forth. It should be understood that these examples are for illustrative purposes only. Therefore, they should not limit the scope of this invention in any way.

EXAMPLES

Example 1

Preparation of OMVs Expressing *Streptococcus* CPS14 and *Burkholderia* OPS

Construction of *S. pneumoniae* Serotype 14 Capsule Plasmid, pNLP80

Figure 1B:
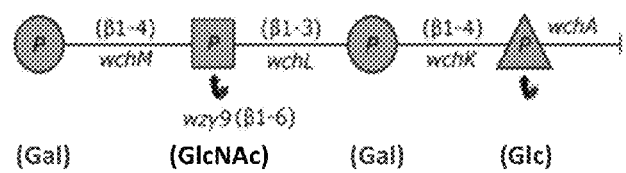
FIG. 1B schematically depicts the cps locus of S. pneumoniae serotype 14 (CPS14), which encodes the enzymes responsible for synthesis of capsule glycan CPS14.
Figure 1C:
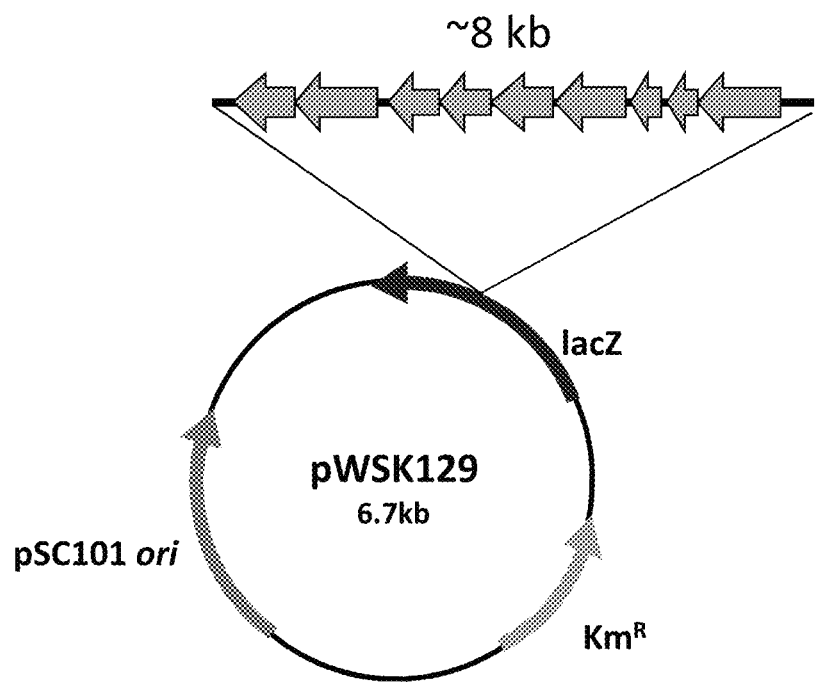
FIG. 1C schematically depicts plasmid pNLP80, which was prepared from cloning the CPS14 locus (starting at the wchA gene) into pWSK129.
Figure 2:
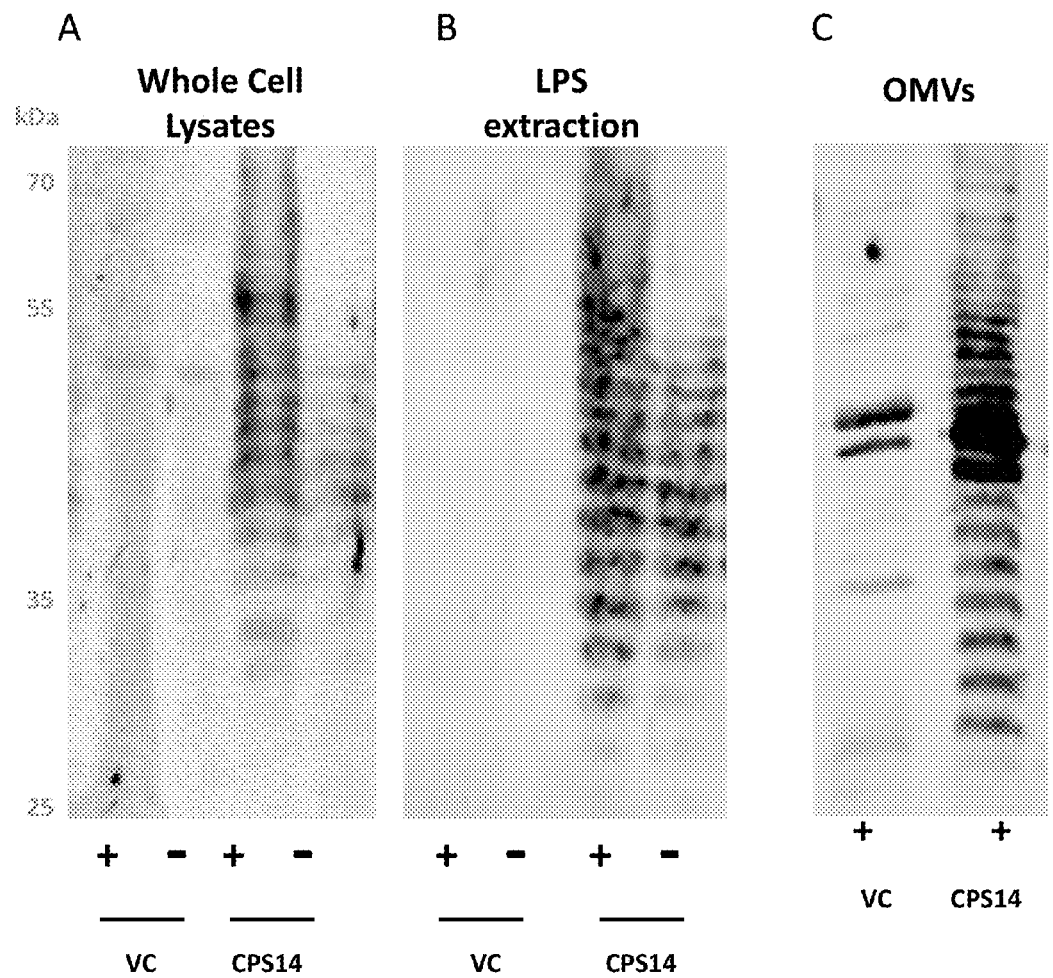
FIGS. 2A, 2B and 2C show photographs of Western blots using whole cell lysates (2A), LPS extracts (2B) and OMVs (2C) from E. coli CLM37 transformed with pNLP80 and induced with IPTG.

*S. pneumoniae* capsule from serotype 14 (CPS14; FIG. 1A) was used in this study. The enzymes responsible for the synthesis of capsule in most *S. pneumoniae*, including serotype 14, are encoded in a single genetic locus (FIG. 1B). The gene cluster responsible for the synthesis of CPS14 (excluding the regulatory genes) was cloned via a 3-way ligation method. Two separate fragments of the CPS14 locus were amplified using a high fidelity polymerase (iProof™, BioRad). Fragment 1 amplified the wchA-wchM region using the forward primer (5'-ATAGAGCTCATGGA-TAAAAAGGATTGGAAAT-3'; SEQ ID NO:1) and reverse primer (5'-TTAAGAAATTCATCCTCATACAA-3; SEQ ID NO:2). Fragment 2 amplified the wchM-wciY region using the forward primer (5'-CTGGTCAACAAAT-ATTAGAAAAA-3; SEQ ID NO:3) and reverse primer (5' ATACTCGAGATTCTTTCTGTAAACTCCAAAAA-3; SEQ ID NO:4). The underlined sequences denotes SacI and XhoI restriction enzyme sites, respectively. The PCR fragments 1 and 2 were both designed to include the native HindIII site within the wchM gene, thus, after a HindIII RE digest, the two fragments were compatible and reconstituted the wchM gene after ligation. Both fragments were successfully amplified and digested with SacI/HindIII (fragment 1) or HindIII/XhoI (fragment 2) and cloned into the plasmid vector pBBR1MCS-2, which was double digested with SacI and XhoI, generating pBBR1MCS-CPS14. The cloned CPS14 locus was confirmed by restriction enzyme digests and sequencing. For proper expression of the CPS14 locus in *E. coli*, the CPS14 locus was subcloned into pWSK129. The wchA-wciY CPS14 fragment was cleaved from pBBR1MCS-CPS14 using SacI and XhoI restriction enzymes. pWSK129 was digested with SacI and SalI restriction enzymes. As XhoI and SalI generate compatible sticky ends, the wchA-wciY fragment was ligated into pWSK129. The resulting plasmid, named pNLP80 (FIG. 1C), was introduced in *E. coli* strain CLM37. This strain does not synthesize O antigen due to a mutation in the wecA gene. The capsular polysaccharide is, as the O antigen, synthesized onto the lipid carrier undecaprenyl-pyrophosphate. Exploiting the relaxed specificity of the WaaL ligase, which normally transfers the O antigen onto the lipid A-core, the CPS14 was assembled onto the LPS of *E. coli*. This was confirmed by western blots, of whole cell lysates and LPS extractions from the transformed *E. coli* CLM37 following introduction of isopropyl β-D-1-thiogalactopyranoside (IPTG) to induce expression, using an antibodies against *Streptococcus* CPS14 (FIG. 2).

Construction of *Burkholderia pseudomallei* O Polysaccharide Plasmid, pEQ3

Figure 4A:
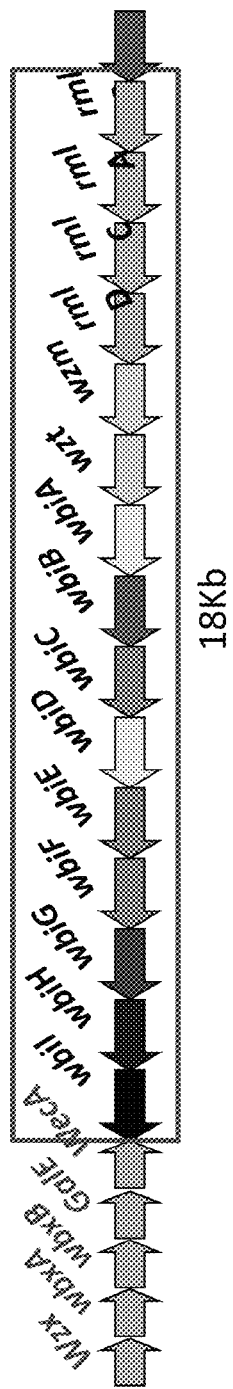
FIG. 4A schematically depicts locus of Burkholderia pseudomallei, which encodes the enzymes responsible for synthesis of its O antigen (O-PS)
Figure 4B:
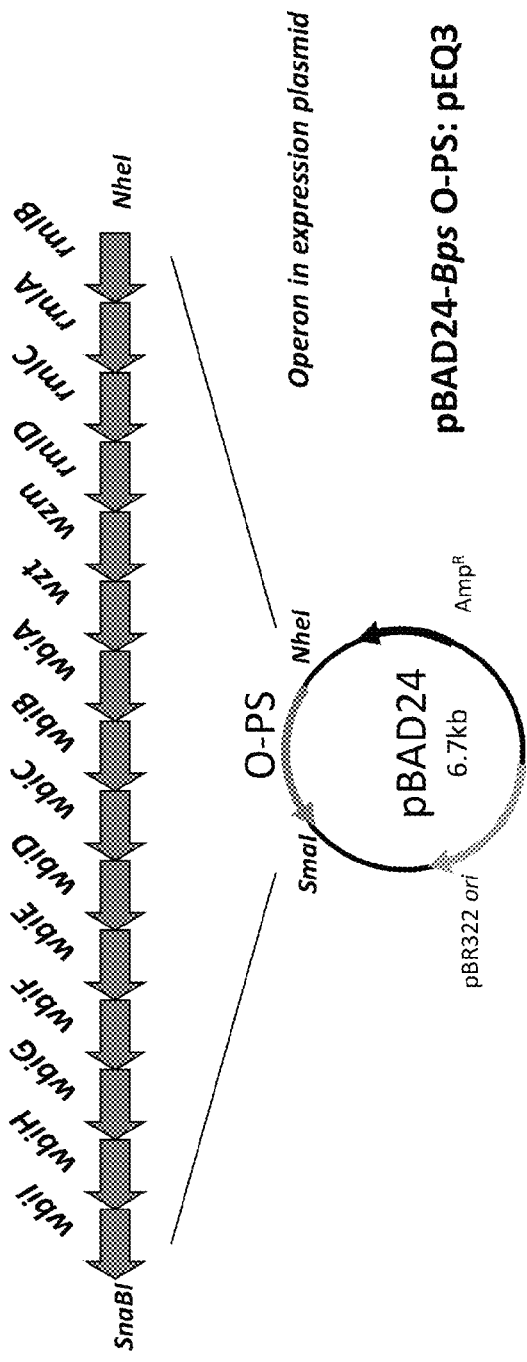
FIG. 4B schematically depicts plasmid pEQ3, which was prepared from cloning the locus for B. pseudomallei O antigen production (starting at the rmlB gene) into pBAD24.

The enzymes responsible for production of the O polysaccharide (OPS) of *B. pseudomallei* K96243 is expressed from a 18 kb locus (FIG. 4A). This locus has been previously cloned into pCC1FOS. For expression in *E. coli* cells, the 18 kb OPS locus was subcloned into pBAD24 using NheI and SnaBI restriction enzymes. The resulting plasmid, pEQ3 (FIG. 4B), was introduced into *E. coli* EPI300 strain where OPS expression was observed.

Figure 3:
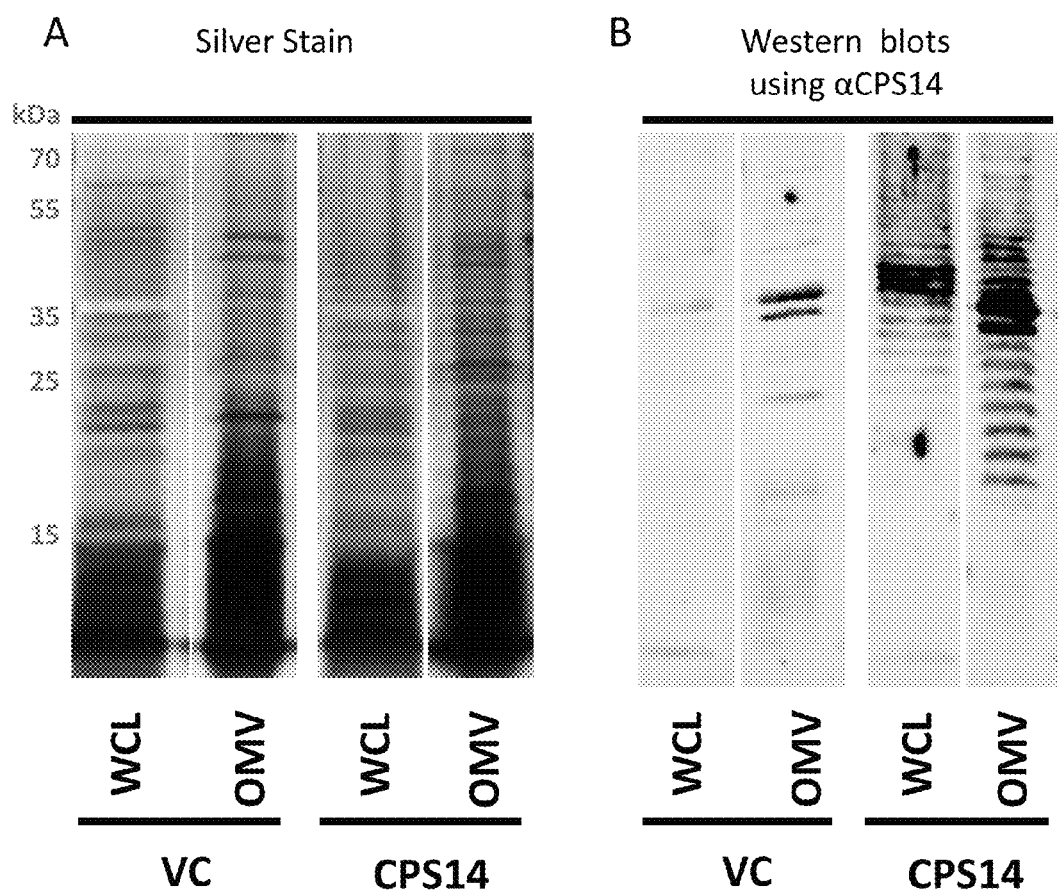
FIGS. 3A and 3B show photographs of a silver stain (3A) and a Western blot (3B) using whole cell lysates and OMVs from E. coli CLM37 transformed with pWSK129 ("VC") or pNLP80 ("CPS14") and induced with IPTG.
Figure 5:
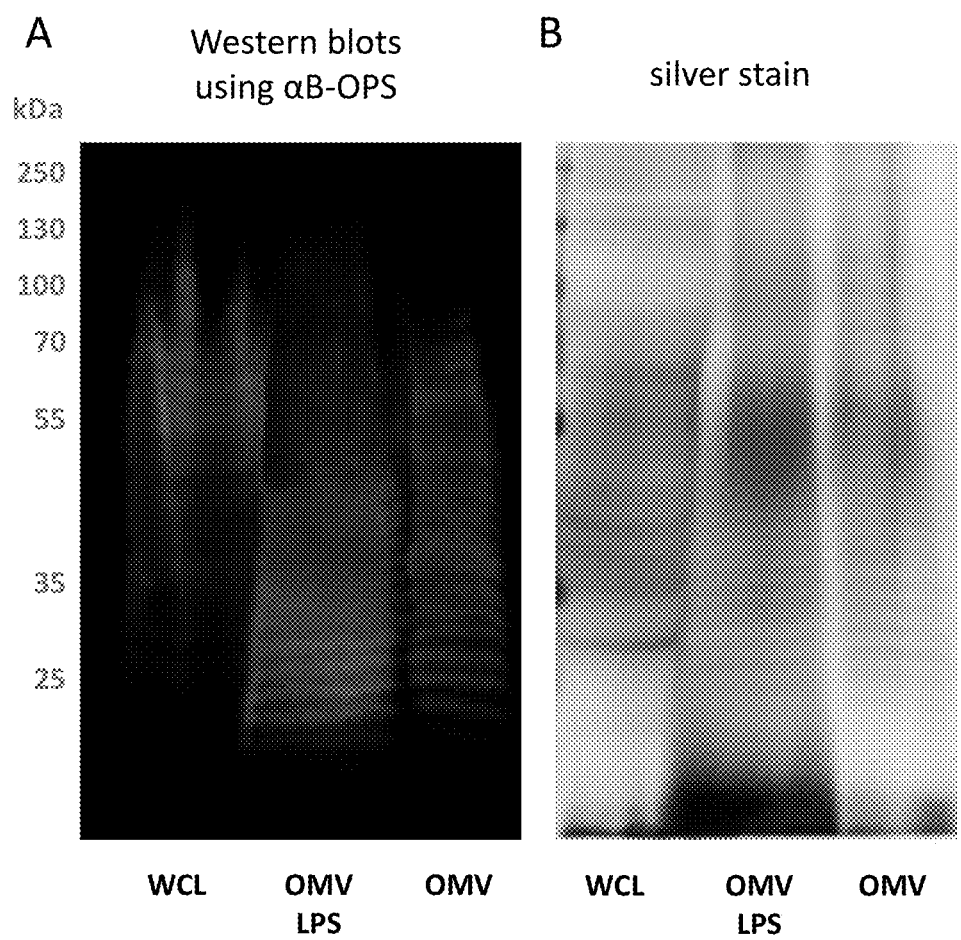
FIGS. 5A and 5B show photographs of a Western blot (5A) and a silver stain (5B) using whole cell lysates and OMVs (with LPS extraction) and OMVs from E. coli EPI300 transformed with pEQ3 and induced with arabinose.

Isolation of OMVs from *E. coli* Expressing *Streptococcus* CPS 14 and *Burkholderia* OPS OMVs were isolated following the protocol described by Haurat et al. (Haurat M F, Aduse-Opoku J, Rangarajan M, Dorobantu L, Gray M R, Curtis M A, Feldman M F. Selective sorting of cargo proteins into bacterial membrane vesicles. J. Biol. Chem. 2011:286(2):1269-76). Briefly, *E. coli* strains harbouring pNLP80, pEQ3, and the respective vector control plasmids were grown at 37° C. overnight with shaking in 50 mL of Luria-Bertani (LB) broth plus appropriate antibiotics. The following day, each culture was subcultured (1:100) into 1 L LB broth plus antibiotics and grown at 37° C. with shaking for 2 h ($OD_{600}$~0.2). To induce *Streptococcus* CPS14 expression, 0.1 mM IPTG was added to the media. To induce expression of *Burkholderia* OPS, 0.2% arabinose was added to the culture. The cultures were grown for an additional 26 h at 37° C. with shaking. After incubation, cells were harvested by centrifugation at 14K rpm for 15 min and the supernatant was collected. The supernatants were filtered twice through 0.44 μm and 0.2 μm filters to remove any residual whole cells. The filtered supernatants were ultracentrifuged at 42K rpm for 3 h at 4° C. The OMV pellets were collected, washed with phosphate buffered saline (PBS), and lyophilized overnight. The OMV preparations were resuspended in 100 μL of distilled water. Presence of LPS containing *Streptococcus* CPS14 and *Burkholderia* OPS was confirmed by silver stain and western blot using an antibodies against *Streptococcus* CPS14 (FIGS. 3A and 3B) and *Burkholderia* OPS, respectively (FIGS. 5A and 5B).

Example 2

Murine Studies with OMV-CPS14

Figure 11:
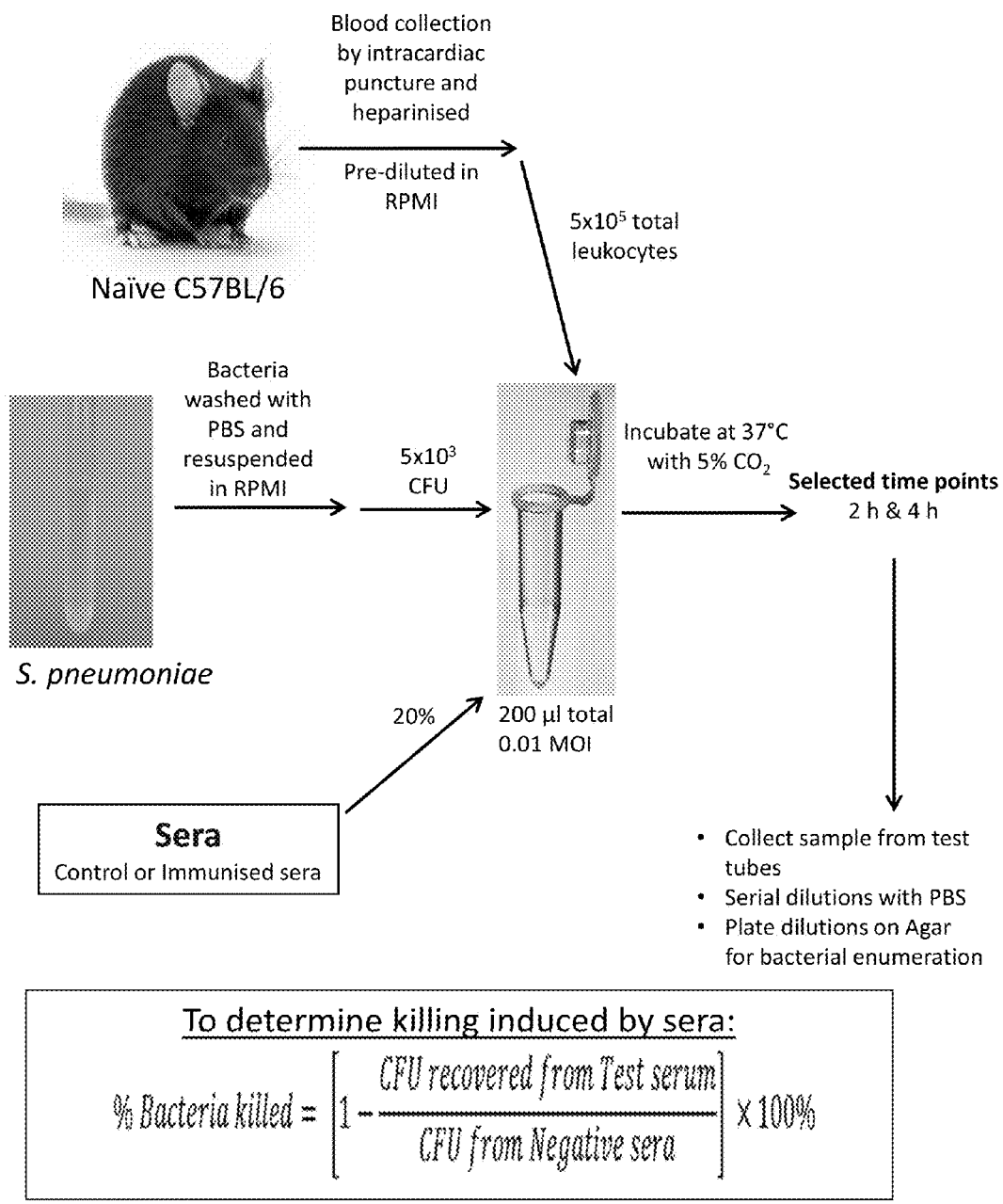
FIG. 11 depicts a strategy for OPA assays in mice.

FIG. 11 shows a strategy for OPA assays using murine whole blood.

Figure 6:
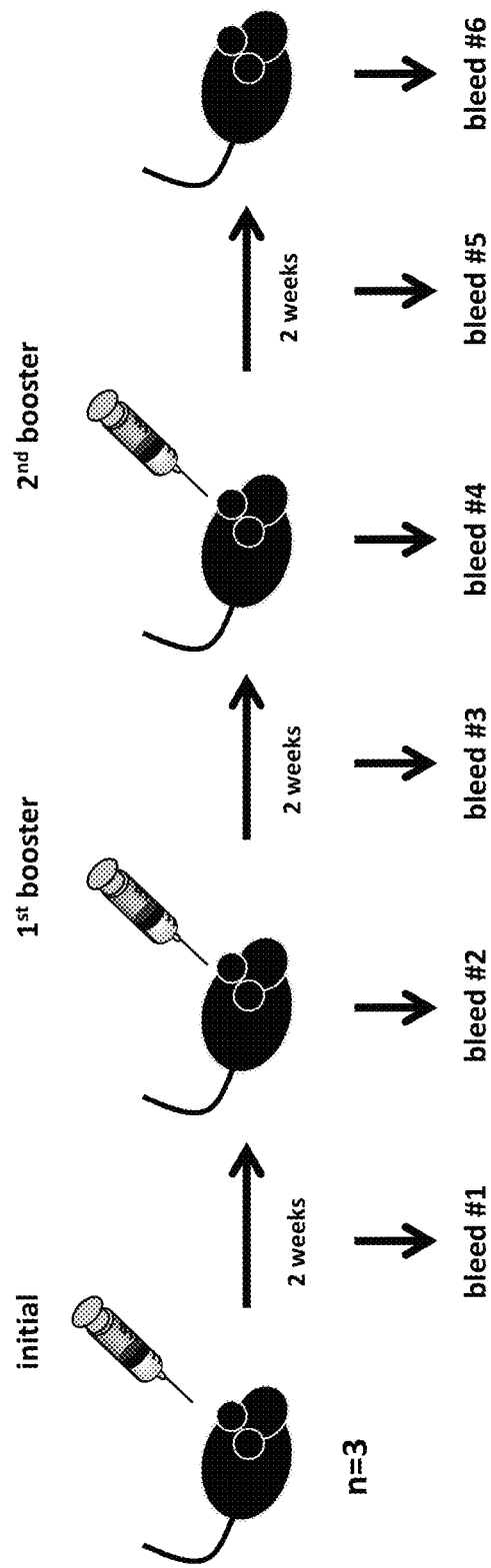
FIG. 6 schematically depicts the inoculation process used to test immunogenicity OMVs displaying CPS14 in mice.
Figure 7:
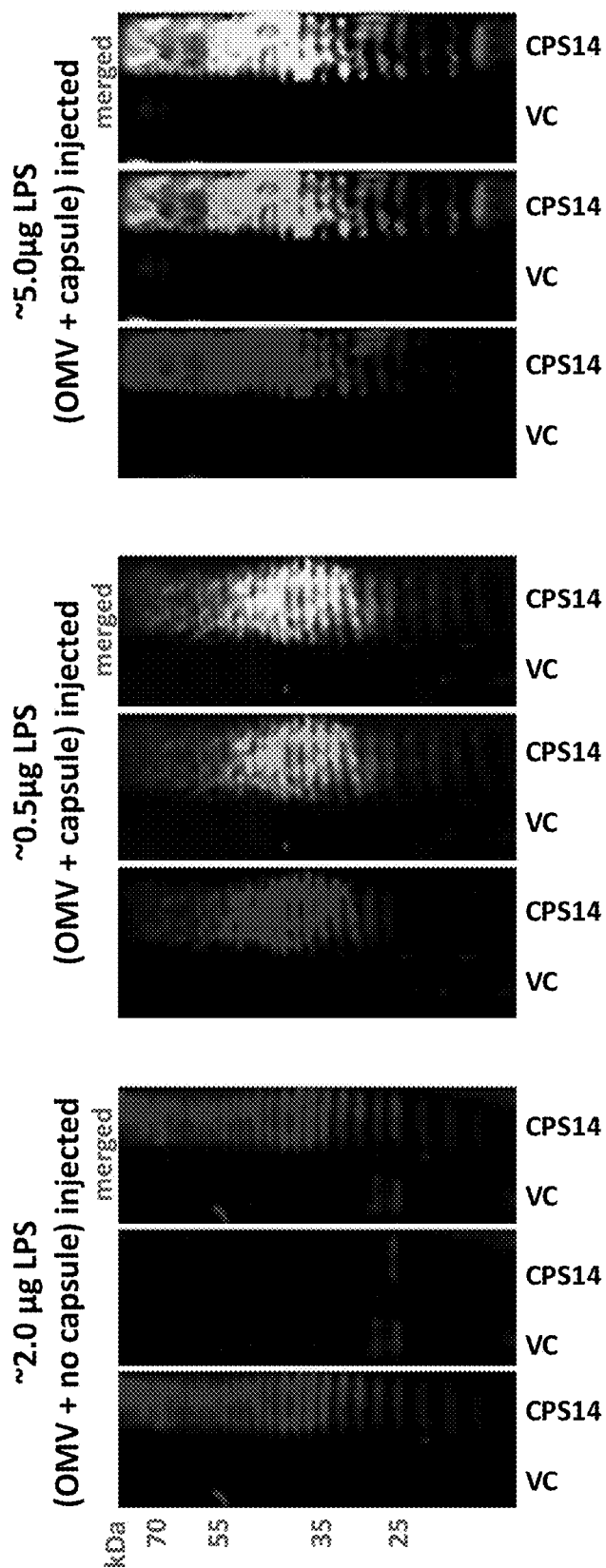
FIGS. 7A, 7B and 7C show photographs from Western blots to identify the presence of antibodies against CPS14 in mice inoculated with OMV from E. coli cells expressing CPS14 ("CPS14") and not expressing CPS14 ("VC"), the Western blots were performed using antibodies against CPS14 (red) and antibodies specific for mice sera (green)
Figure 8:
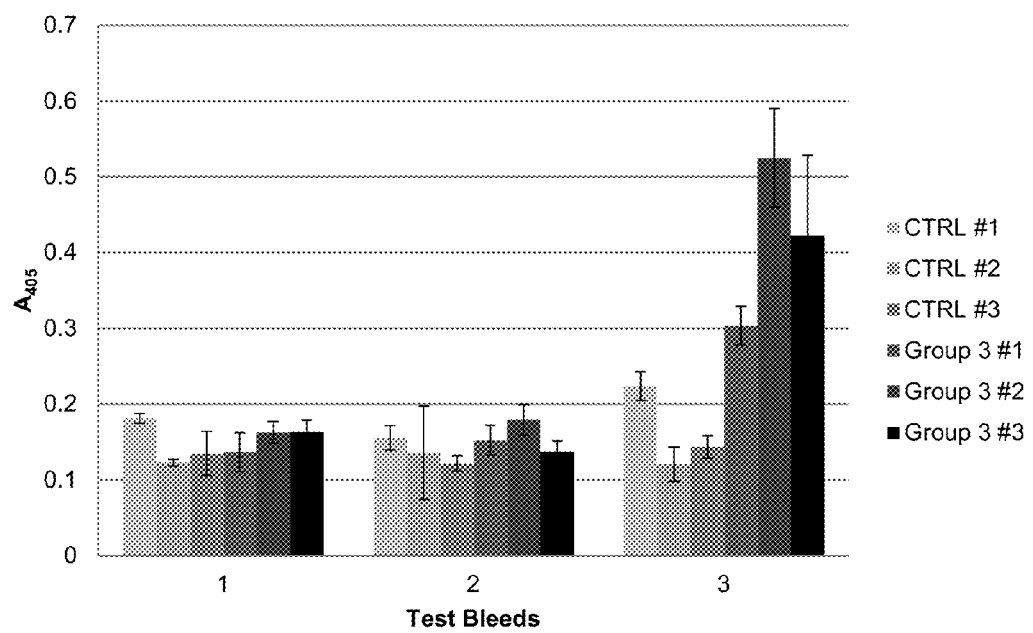
FIG. 8 graphically depicts the results from ELISAs performed to confirm that the mice sera from mice inoculated with OMV from E. coli cells expressing CPS14 could react with Streptococcus pneumonia serotype 14 directly.

To test the immunogenicity of the OMV, three groups of three mice each were injected with different amounts of OMVs from *E. coli* cells expressing CPS14 (CLM37 with pNLP80; groups 0.5 μg, 2.0 μg and 5.0 μg of calculated LPS). A control group received OMV (2.0 μg of calculated LPS) from *E. coli* cells not expressing CPS14 (CLM37 with pWSK129). The strategy for the inoculation is depicted in FIG. 6. One week after the first booster, sera of the three groups were obtained. The presence of antibodies against CPS14 was analyzed by Western-blot. OMV preparations digested with proteinase K were analyzed using 1/500 dilutions of the mice sera (FIG. 7). Anti CPS14 was used as positive control. This experiment studied four groups of mice: the control group; group 1, which received ~0.5 μg of LPS/~0.25 μg capsule; group 2, which received ~2.0 μg of LPS/~1.0 μg capsule; and group 3, which received ~5.0 μg of LPS/~2.5 μg capsule. The results showed that mice receiving OMV containing 0.5, 2.0 and 5.0 μg of LPS were all able to mount an IgG response directed against CPS14, as the bands corresponding to CPS14 were detected with the sera of animals inoculated with OMV containing CPS14 (FIG. 7, only 0.5 and 5.0 μg groups are shown). The sera of the mice that received OMV without CPS14 did not react towards the LPS containing the CPS14.

An enzyme-linked immunosorbant assay (ELISA) was performed to determine whether the mice sera could react with *Streptococcus pneumonia* serotype 14 directly. *S. pneumonia* was grown overnight on blood agar plates at 37° C. with 5% $CO_2$ aerobic conditions. The next day the cells were scraped from the agar plate, resuspended in PBS, and heat inactivated by incubation at 60° C. for 2 h. The cells were diluted to OD600~0.6/mL in PBS with protease inhibitor and 100 μL were seeded into ELISA 96 well plate. The plate was incubated overnight at 4° C. The following day, the wells were washed three times with PBS before blocking with 2.5% skim milk for 2 h. The wells were washed three times with PBS and blotted dry. 100 μL of mice sera (1:500 dilution) was added to each well and the plate was incubated at room temperature for 1 h. After incubation, the wells were washed again three times with PBS and 100 μL of anti-mouse-alkaline phosphatase antibody was added to each well and incubated at room temp for 1 h. After the secondary antibody incubation, the wells were washed again three times with PBS and blotted dry. 100 μL of p-nitrophenyl phosphate was added to each well and the plate was incubated at 37° C. for 1 h followed by reading the absorbance at 405 nm on a BioTek™ plate reader. The results showed that after the first booster injection (test bleed #3), the mice sera with OMV expressing CPS14 reacted towards the *S. pneumoniae* capsule, whereas the mice sera with OMV not expressing CPS14 failed to react with the *S. pneumoniae* cells.

Figure 9:
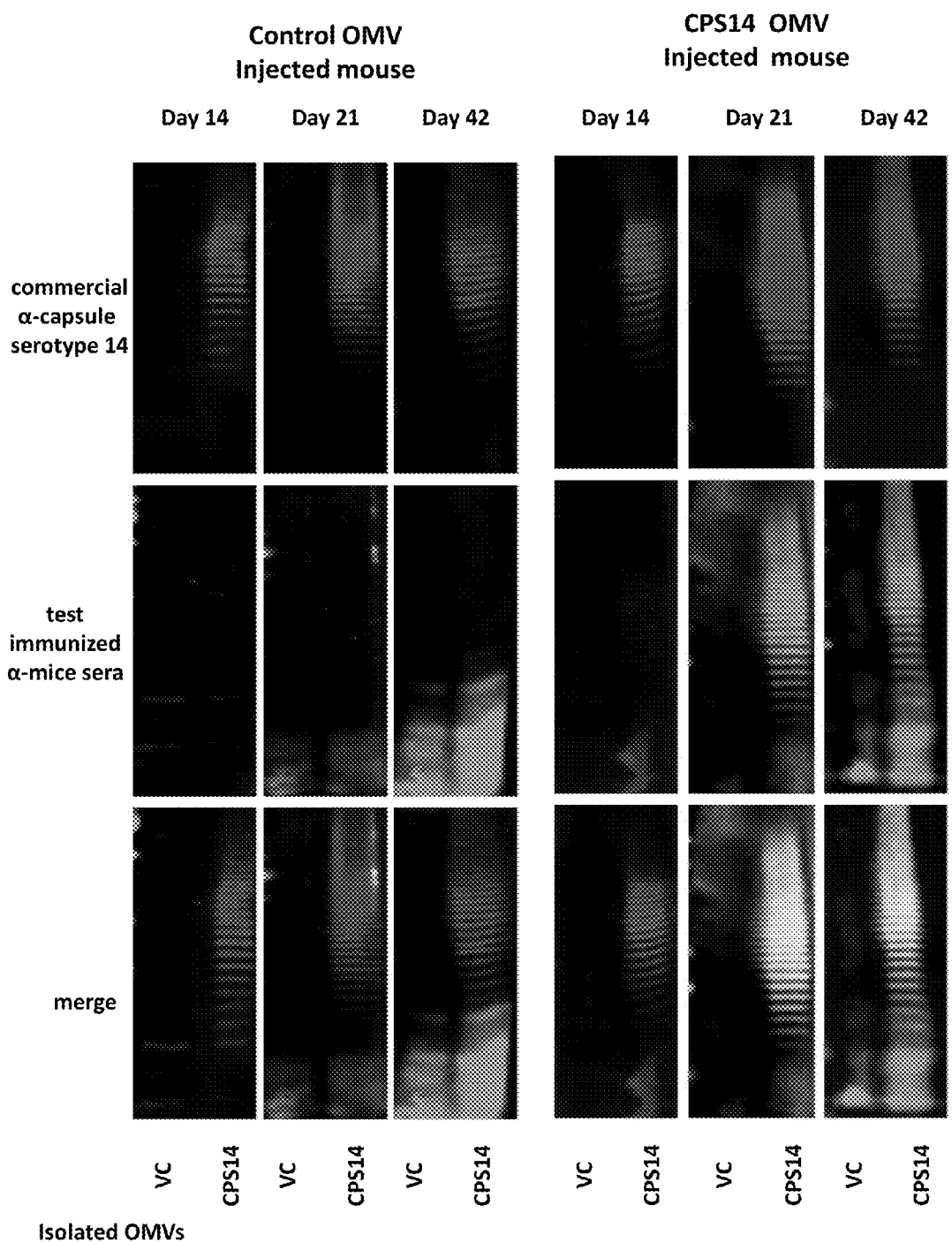
FIG. 9 shows the results of analyzing the immune response in sera of mice immunized with OMV.

FIG. 9 shows that the sera of mice immunized with OMV carrying the *Streptococcus* capsule elicit and IgG immune response. The sera from mice that receive the glycoengineered OMV recognize the capsule.

Figure 10:
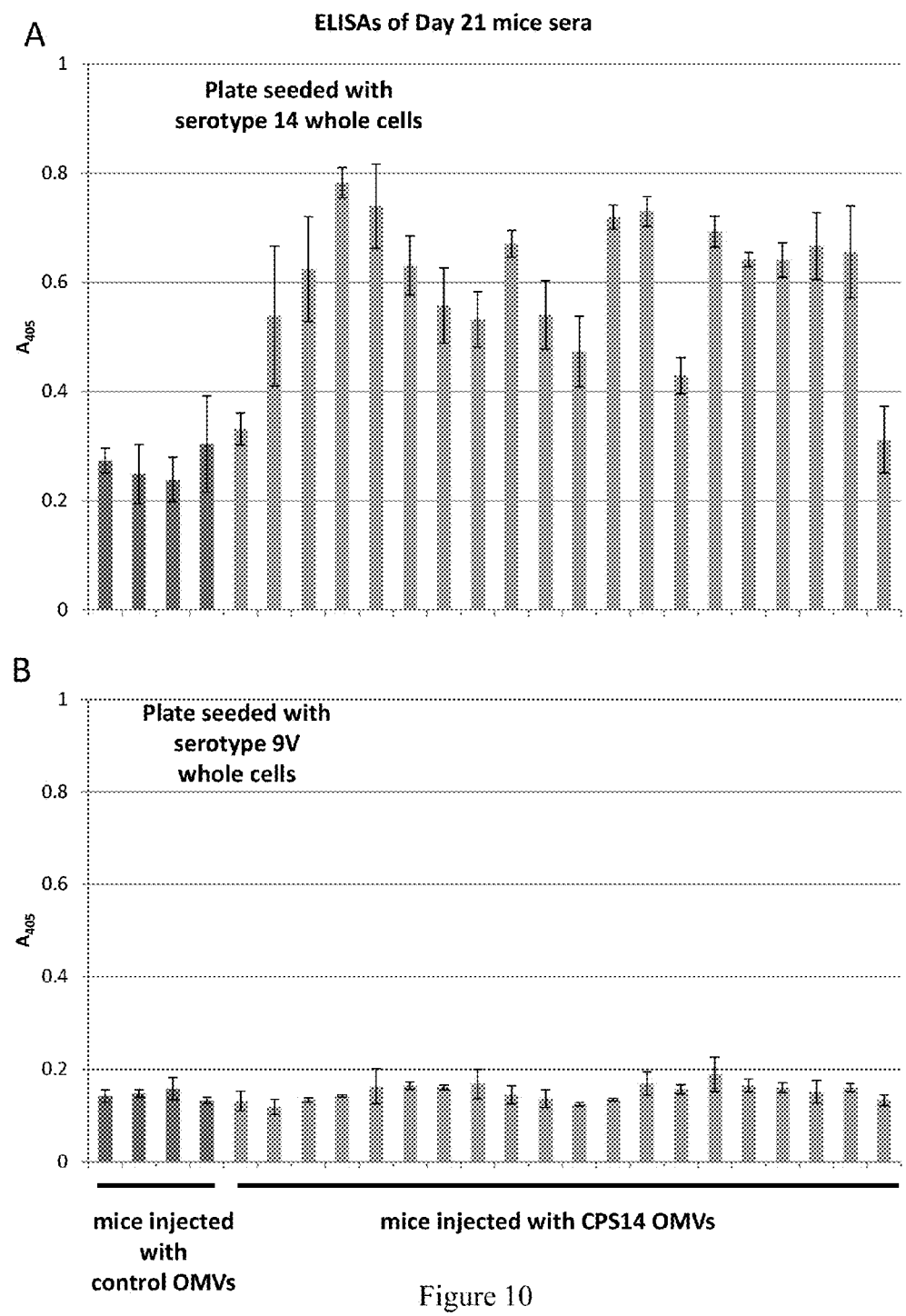
FIGS. 10A and 10B graphically depict results from ELISAs performed to confirm that sera of mice that received OMV with the capsule 14 only recognize the corresponding bacteria.

FIGS. 10A and 10B show results from ELISA in which *Streptococcus* bacteria from serotype 14 (FIG. 10A) or 9V (FIG. 10B) are immobilized in the plates and the sera of mice that received OMV with the capsule 14 only recognize the corresponding bacteria. This illustrates that the glycans represent immunoreactive material and that it is serotype specific.

Figure 12:
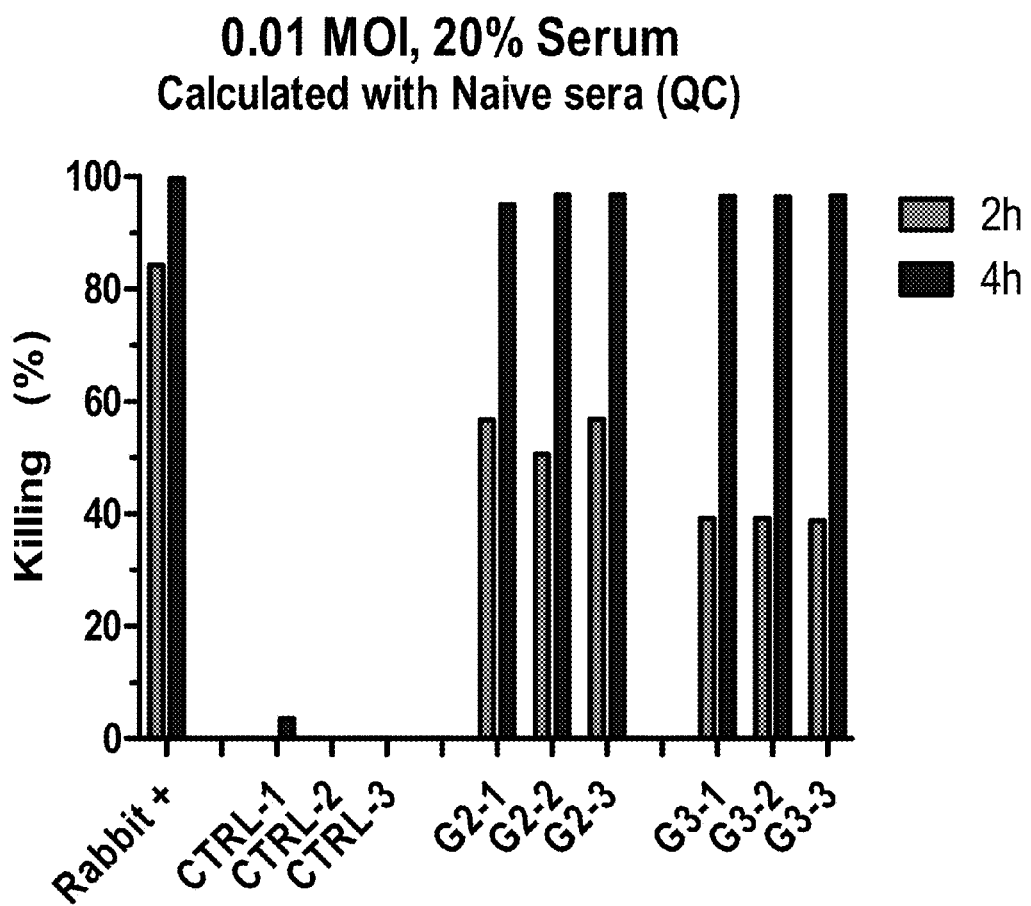
FIG. 12 graphically depicts that the sera of mice immunized with glycoengineered OMVs (geOMVs) can assist mice leukocytes in killing bacteria.

FIG. 12 shows that the sera of mice immunized with geOMV can assist mice leukocytes in killing the bacteria, which is particularly advantageous for ensuring immuno-protection. The assay demonstrates a protective effect with sera from OMV+CPS14.

Figure 13:
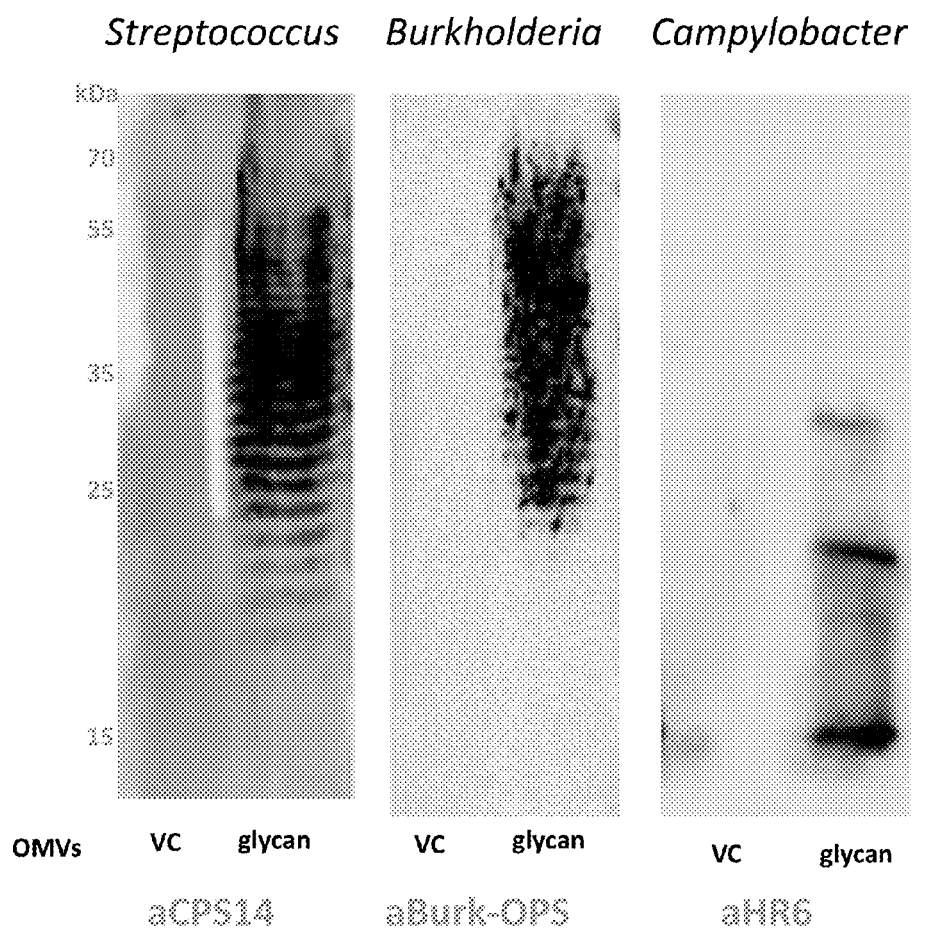
FIG. 13 shows Western blots displaying sugars from different bacteria (Burkholderia and Campylobacter) using the present OMV.

FIG. 13 shows Western blots we can also have OMV with other sugars, like the O antigen of *Burkholderia pseudomallei* or the *Campylobacter jejuni* glycan. Particularly, it can be seen that sugars from different bacteria and pathways can be displayed and that geOMVs can be generated with other glycan units.

This study demonstrated that glycoengineered OMV can be used successfully to elicit an immune response against a recombinantly expressed glycan, including the capsule of a Gram positive bacterium, which does not produce OMVs.

In summary, as described herein, glycoengineered OMVs (geOMVs) are produced. Isolated geOMVs displaying the *S. pneumoniae* serotype 14 capsule were introduced into a murine host model and shown to elicit a specific immune response against the *S. pneumoniae* serotype. In addition, opsonophagocytic killing assays show that sera obtained from mice immunized with these geOMVs elicit a protective affect against whole cell *S. pneumoniae*. Furthermore, the geOMVs can be generated to display a diverse set of bacterial carbohydrates, including O antigens from Gram-negative bacteria such as *Burkholderia pseudomallei* and the N-glycan of *Campylobacter jejuni*. geOMVs may replace or complement the polysaccharide-based vaccines currently employed.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. An outer membrane vesicle (OMV) obtained from a recombinant, gram-negative bacteria comprising heterologous DNA capable of producing a capsular polysaccharide derived from a gram-positive bacteria, wherein the recombinant bacteria presents the capsular polysaccharide on its surface as a component of lipopolysaccharide (LPS) which is in incorporated in the OMV, wherein all or a portion of the naturally-occurring O antigen is replaced.

2. A vaccine comprising the outer membrane vesicle according to claim 1.

3. The vaccine of claim 2, which additionally comprises a pharmaceutically acceptable carrier, diluent, excipient or adjuvant.

4. The vaccine of claim 2, which comprises a combination of more than one of the outer membrane vesicles, wherein each of the more than one outer membrane vesicles expresses a different heterologous glycan at its surface.

5. The outer membrane vesicle of claim 1, wherein the gram-positive bacteria is *Staphylococcus aureus* or *Streptococcus pneumoniae*.

6. The outer membrane vesicle of claim 1, wherein the capsular polysaccharide is ligated to lipid A of a lipopolysaccharide (LPS).

7. The outer membrane vesicle of claim 1, which do not express its naturally occurring O antigen.

8. The outer membrane vesicle of claim 1, which is recombinant *Escherichia coli*.

* * * * *